United States Patent [19]
Mond et al.

[11] Patent Number: 5,932,427
[45] Date of Patent: *Aug. 3, 1999

[54] IN VITRO ASSAY SYSTEM FOR IDENTIFYING COMPOSITIONS USEFUL FOR STIMULATING B CELLS

[75] Inventors: James J. Mond, Potomac; Clifford M. Snapper, Kensington, both of Md.

[73] Assignee: Henry M. Jackson Foundation for the Advancement of Military Medicine, Rockville, Md.

[ * ] Notice: This patent issued on a continued prosecution application filed under 37 CFR 1.53(d), and is subject to the twenty year patent term provisions of 35 U.S.C. 154(a)(2).

[21] Appl. No.: 08/468,475

[22] Filed: Jun. 6, 1995

Related U.S. Application Data

[63] Continuation of application No. 08/315,492, Sep. 30, 1994, abandoned, which is a continuation-in-part of application No. 08/150,510, Nov. 10, 1993.

[51] Int. Cl.$^6$ ..................................................... G01N 33/53
[52] U.S. Cl. ............................ 435/7.24; 435/7.8; 435/7.1
[58] Field of Search ................................ 435/7.24, 7.8, 435/7.1; 436/547; 530/387.1, 351

[56] References Cited

U.S. PATENT DOCUMENTS

| | | |
|---|---|---|
| 4,496,538 | 1/1985 | Gordon . |
| 4,673,574 | 6/1987 | Anderson . |
| 4,959,455 | 9/1990 | Clark et al. . |
| 5,073,627 | 12/1991 | Curtis et al. . |
| 5,128,450 | 7/1992 | Urdal et al. . |
| 5,162,111 | 11/1992 | Grabstein et al. . |
| 5,166,322 | 11/1992 | Shaw et al. . |
| 5,186,931 | 2/1993 | Kishimoto et al. . |
| 5,196,320 | 3/1993 | Gillies . |
| 5,273,889 | 12/1993 | Potter et al. . |
| 5,334,379 | 8/1994 | Pillai et al. . |
| 5,359,035 | 10/1994 | Habermann . |
| 5,476,929 | 12/1995 | Briles et al. . |
| 5,556,946 | 9/1996 | Fujisawa et al. . |

FOREIGN PATENT DOCUMENTS

| | | |
|---|---|---|
| 0 351 876 | 1/1990 | European Pat. Off. . |
| WO 95/13089 | 5/1995 | WIPO . |

*Primary Examiner*—Paula K. Hutzell
*Assistant Examiner*—Heather A. Bakalyar
*Attorney, Agent, or Firm*—Finnegan, Henderson, Farabow, Garrett & Dunner, L.L.P.

[57] ABSTRACT

The invention describes compositions comprising adding granulocyte-macrophage colony stimulating factor (GM-CSF), interleukin-3 (IL-3), or a combination thereof useful for stimulating the release of antibody by B cells. Methods of using the compositions, pharmaceutical compositions, vaccines, and vaccines adjuvants are also described. In addition, this invention describes an assay system useful for identifying compounds capable of stimulating the release of antibody by B cells.

8 Claims, 7 Drawing Sheets

IN VITRO ASSAY SYSTEM FOR IDENTIFYING COMPOSITIONS USEFUL FOR STIMULATING B CELLS

CROSS-REFERENCE TO RELATED APPLICATION

This is a continuation of prior application Ser. No. 08/315,492, filed Sep. 30, 1994, now abandoned, which is a continuation-in-part of application Ser. No. 08/150,510, filed Nov. 10, 1993, herein incorporated by reference.

GOVERNMENT INTEREST

The invention described herein may be manufactured, licensed, and used for governmental purposes without the payment of any royalties to the inventors or assignee.

FIELD OF THE INVENTION

This invention relates to compositions comprising granulocyte-macrophage colony stimulating factor (GM-CSF) and interleukin-3 (IL-3), either alone or in combination, and compositions of GM-CSF and IL-3, either alone or in combination, along with interferon-$\gamma$ (IFN-$\gamma$). The compositions are useful for stimulating the release of antibodies by mammalian B lymphocytes. This invention also relates to an in vitro assay system for identifying compositions that stimulate the release of antibodies by B lymphocytes.

Stimulation of antibody release by B lymphocytes is useful in the battle to prevent, treat, and/or ameliorate the deleterious effects of infection and disease. This usefulness extends to adjuvants for bolstering mammalian immune responses under normal conditions and under immunosuppressed or immunocompromised conditions. The novel compositions can also be used in conjunction with other immunotherapies to bolster the human immune system.

BACKGROUND OF THE INVENTION

The human immune system comprises numerous different types of cells having overlapping functions which together act to protect the human body against sickness and disease. The cells of the immune system have complex multiple functions and interconnecting relationships.

GM-CSF, IL-3, and IFN-$\gamma$ are all cytokines. "Cytokines" are a class of compounds which regulate responses of cells of the immune system, such as B and T lymphocyte cells ("B cells" and "T cells") and natural killer ("NK") cells. A "cytokine" is a generic term for a nonantibody protein released by certain cell populations on contact with an inducer and which acts as an intercellular mediator. A "lymphokine" is a soluble substance released by sensitized lymphocytes on contact with specific antigen or other stimuli which helps effect cellular or humoral immunity.

The terms "cytokine" and "lymphokine" have become interchangeable. In an attempt to simplify the nomenclature of these compounds, a group of participants at the Second International Lymphokine Workshop held in 1979 proposed the term "interleukin," abbreviated "IL," to develop a uniform system of nomenclature based on the ability of the proteins to act as communication signals between different populations of leukocytes.

To date, 21 different cytokines, most but not all of which are produced by T cells, have been identified. Each has a distinct molecular configuration and performs a different task. A number of the known cytokines have been shown to have a demonstrable activity on B cells. In vitro, the lymphokines IL-1, IL-2, IL-4, IL-5, IL-6, IL-10, IFN-$\gamma$, and TGF-$\beta$ (transforming growth factor $\beta$) have been shown to enhance B cell proliferation, immunoglobulin secretion, or to otherwise play a role in influencing the subclass of secreted Ig. Depending on the system being studied, addition of either one or a number of the above lymphokines has been shown to increase in vivo antibody production or to alter the isotype (i.e., IgG, IgM, IgE, IgA, etc.) of secreted antibody. Among the lymphokines reported to influence B cell proliferation include IL-1, IL-2, IL-4, and IL-10, and those reported to influence B cell differentiation and Ig secretion include IL-2, IL-5, IL-6, TGF-$\beta$, and IFN-$\gamma$.

None of the reported cytokines which enhance Ig secretion in vitro have been shown to play a prominent role in vivo. Thus, infusion of monoclonal antibodies specific for IL-2, IL-5, IL-6, or IFN-$\gamma$ does not significantly suppress antigen-stimulated antibody production. This suggests that, under physiologic conditions, B cell differentiation depends solely on direct T cell interaction, or that other as yet unknown cytokines mediate this step.

While immune responses to antigens that stimulate T cell activation (the so-called T dependent antigens or "TD antigens") could rely on direct T cell interactions with B cells to effect Ig secretion, this is not the case with antigens that are unable to induce T cell activation. Antigens which are T cell independent ("TI antigens") induce high levels of antibody production in the absence of direct or even indirect T cell help. Thus, the events that regulate B cell differentiation and immunoglobulin secretion to TI antigens must rely on other as yet undefined pathways. Since B cell differentiation leading to immunoglobulin secretion is the final event which underlies a competent humoral antibody system, defining the events or cytokines which regulate this step is invaluable in designing methods for amplifying or suppressing an immune response.

To facilitate a quick appreciation of the invention, the following provides a brief description of the primary known functions of immunoglobulin, antibodies, lymphocytes, B cells, T cells, and NK cells as background. Also provided is a brief summary of the known activities of the cytokines reported to influence B cell proliferation or antibody secretion, namely IL-1, IL-2, IL-4, IL-5, IL-6, IL-10, TGF-$\beta$, and IFN-$\gamma$. A summary of the known activities of GM-CSF and IL-3 is also provided. Reference materials include *Fundamental Immunology*, Second Edition, William E. Paul, M. D., ed. (Raven Press, New York 1989); *Fundamental Immunology*, Third Edition, William E. Paul, M.D., ed. (Raven Press, New York 1993); *Interferon: Principles and Medical Applications*, S. Baron et al., eds. (The University of Texas Medical Branch at Galveston, Galveston, Texas 1992); *The Cytokine Handbook*, Angus Thomson, ed. (Academic Press Inc., San Diego, Calif. 1992); and *The Cytokine Handbook*, Second Edition, Angus Thomson, ed. (Academic Press Inc., San Diego, Calif. 1994), all of which are specifically incorporated by reference.

Mammals, including man, are confronted on a daily basis with a myriad of organisms. A major component of the immune system that plays an essential role in protecting the host against infection by these organisms is the humoral antibody. Antibodies are protein molecules, also known as immunoglobulins, which have exquisite specificity for the foreign particle which stimulates their production. For example, systemic infection with "bacteria A" will induce antibodies that bind with a high avidity to "bacteria A" but not to "bacteria B." Similarly, "bacteria B" will induce anti-"bacteria B" antibodies which do not cross-react with "bacteria A."

Immunoglobulin (Ig) is a class of structurally related proteins consisting of two pairs of polypeptide chains, one pair of light (L) [low molecular weight] chains ($\kappa$ or $\lambda$), and one pair of heavy (H) chains ($\gamma$, $\alpha$, $\mu$, $\delta$, and $\epsilon$), all four linked together by disulfide bonds. Both H and L chains have regions that contribute to the binding of antigen and that are highly variable from one Ig molecule to another. In addition, H and L chains contain regions that are nonvariable or constant. On the basis of the structural and antigenic properties of the H chains, Ig's are classified as IgG, IgA, IgM, IgD, and IgE isotypes. Subclasses of IgG's, based on differences in the H chains, are referred to as IgG1, etc.

Lymphocytes are white blood cells formed in lymphatic tissues throughout the body, such as lymph nodes, spleen, thymus, tonsils, Peyer's patches (small intestine tissue), and sometimes in bone marrow. Individual lymphocytes are specialized in that they are committed to respond to a limited group of structurally related antigens. This commitment, which exists prior to the first contact of the immune system with a given antigen, is expressed by the presence of antigen-specific receptors (i.e., immunoglobulin) on the lymphocyte membrane. The ability of an organism to respond to virtually any antigen is achieved by the existence of a very large number of different clones of lymphocytes, each bearing receptors specific for distinct antigens. In consequence, lymphocytes are an enormously heterogeneous collection of cells.

Lymphocytes differ from one another not only in the specificity of their receptors but also in their functional properties. Two broad classes of lymphocytes are recognized: the B lymphocytes and the T lymphocytes. In addition to these. two classes, lymphoid cells that mediate certain "nonspecific" cytotoxic responses are known. These include natural killer (NK) cells.

B lymphocytes, also known as "B cells," are a type of lymphocyte that derive from hematopoietic stem cells by a complex set of differentiation events that are only partially understood. B cells are precursors of antibody-secreting cells and thus are responsible for the production of immunoglobulins. The cell-surface receptor of B cells is an antibody or immunoglobulin (Ig) molecule specialized for expression on the cell surface. Newly differentiated B cells initially express surface Ig solely of the IgM class. Associated with maturation of a B cell is the appearance of other immunoglobulin isotypes on the surface of the B cell.

To release antibody in response to cytokines, the B cells must first be activated. There are many ways to activate B cells, including cross-linkage of membrane Ig molecules by the antigen (cross-linkage-dependent B cell activation), direct encounter with T cells (helper T cells or helper T cell-associated molecules, such as, for example, CD40 ligand), or encounter with mitogens. In such encounters, the antigen presents epitopes recognized by the B cell's cell-surface Ig.

Because each B cell bears multiple membrane Ig molecules with identical variable regions, optimal membrane-Ig mediated cross-linkage activation is achieved by a high level of cross-linkage of the cell-surface receptors, which requires that the antigen present more than one copy of the epitope that the cell-surface Ig recognizes. Although many simple protein antigens do not have this potential, such a requirement is fulfilled by polysaccharides and other antigens with repeating epitopes, such as surfaces of microbes and DNA. Among these antigens are the capsular polysaccharides of many medically important microorganisms, such as pneumococci, streptococci, and meningococci.

There are much data to show that cross-linkage of membrane Ig can also lead to elimination or inactivation of B cells. In general, it is believed that certain types of receptor cross-linkage events, if they occur in the absence of specific stimulatory signals, lead to inactivation rather than activation. The highly repetitive epitopes expressed on polysaccharides may lead to activation in the absence of costimulation, possibly because of the magnitude of the receptor-mediated stimulation.

T lymphocytes, or "T cells," are thymocyte derived, of immunological importance that is long-lived (months to years), and are responsible for cell-mediated immunity. T cells consist of functionally different populations, known as "helper T cells," "suppressor T cells," and "killer T cells." T cells involved in delayed hypersensitivity and related immune phenomena are also known.

Natural killer cells, or "NK cells," are lymphoid cells that mediate certain "nonspecific" cytotoxic responses. Such nonspecific cytotoxic responses kill certain forms of tumor cells using recognition systems that are different from those used by T or B cells. Killing of one cell type by another through contact interaction constitutes a major effector arm of self-defense of the immune system.

In addition to these cells, other compounds, the cytokines, play a significant role in protecting a host. One group of cytokines is the interleukins.

IL-1 is primarily an inflammatory cytokine, whereas IL-2 and other cytokines are primarily growth factors for lymphocytes. IL-1 is a polypeptide hormone synthesized by monocytes. During inflammation, injury, immunological challenge, or infection, IL-1 is produced and, because of its multiple biological properties, this cytokine appears to affect the pathogenesis of the disease. In animals, IL-1 is a potent. inducer of hypotension and shock. IL-1 acts on the hypothalamus to induce fever and directly on skeletal muscle to promote protein catabolism.

IL-2, also known as T cell growth factor, is a lymphokine and polypeptide hormone produced by both T helper and suppressor lymphocytes. This cytokine has direct effects on the growth and differentiation of T cells, B cells, NK cells, lymphokine-activated killer (LAK) cells, monocytes, macrophages, and oligodendrocytes.

IL-3, also known as multicolony stimulating factor, acts on numerous target cells within the hemopoietic system. This cytokine has the broadest target specificity of any of the haematopoietic growth factors (HPGFs), and can stimulate the generation and differentiation of hemopoietic stem cells (i.e., precursors of blood cells), which give rise to macrophages, neutrophils, eosinophils, basophils, mast cells, megakaryocytes, and erythroid cells.

The relationship between IL-3 and B cells was unclear prior to the invention. In fact, as of 1994, it was believed that the range of target cells of IL-3 did not include cells committed to the T- and B-lymphoid lineages, and that there was no compelling evidence that IL-3 had a significant, direct effect on B-cell development. J. W. Schrader, "Chapter 5: Interleukin-3," *The Cytokine Handbook,* 2nd Ed., Angus Thomson, ed., page 84 (Academic Press, New York, 1994).

Secretion of IL-3 by B cells has not been reported, although IL-3 is synthesized by T cells and mast cells. Several reports demonstrated that IL-3 could induce a modest enhancement of Ig secretion by human B cells activated with SAC (a polyclonal activator) and IL-2. For example, Xia et al., "Human Recombinant IL-3 is a Growth Factor for Normal B Cells," *J. of Immunology,* 148, 491–497 (1992), reported that IL-3 enhanced the proliferation of a population of cells enriched in B cells. Similarly, Tadmori et al., "Human Recombinant IL-3 Stimulates B Cell Differentiation," *J. of Immunol.*, 142, 1950–1955 (1989), reported that IL-3 stimulated IgG secretion from tonsillar cells containing B cells or in a population of peripheral blood-derived enriched B cells activated by bacterial antigen. In addition, Matsumoto et al., "Induction of IgE Synthesis in Anti-IgM-Activated Nonatopic Human B Cells by Recombinant Interleukin-3," *Int. Arch. Allergy Appln. Immunol.*, 89, 24–30 (1989), reported that human recombinant IL-3 augmented IgE synthesis by normal B cells or mixtures of T and B lymphocytes, and that IL-1, IL-2, IL-5, IL-6, GM-CSF, G-CSF, M-CSF, and IFN-$\gamma$ failed to induce IgE synthesis. Matsumoto et al. also note that they could not conclusively identify IL-3 as the factor in the T cell supernatant responsible for inducing IgE synthesis because the activity could not be reversed by the addition of anti-IL-3 antibody.

These results were attributed to an IL-3-mediated enhancement in cell growth. In these studies, B cells were not electronically sorted and thus were not highly purified. Thus, the Ig enhancing effect may reflect the action of IL-3 on many contaminating non-B, non-T cells in the population, and it is therefore not possible to determine from these experiments whether IL-3 was acting directly on the B cell. Further, in prior experiments, B cells were not fractionated according to size. Thus, a possible role for the prior activational state of the B cell was not addressed.

In further contrast to the present invention, Kimoto et al., "Recombinant Murine IL-3 Fails to Stimulate T or B Lymphopoiesis In Vivo, But Enhances Immune Responses To T Cell-Dependent Antigens," *J. of Immunology*, 140, 1889–1894 (1988), reported that mice bearing osmotic minipumps loaded with murine recombinant IL-3 showed no increase in the lymphoid organs of the total number of B and T cells. Furthermore, Kimoto et al. suggested that IL-3 does not act directly on lymphocytes or their precursors, but may potentiate the humoral immune response to T cell-dependent antigens, presumably by acting on accessory cells.

IL-4 is a glycoprotein also known as B cell stimulating factor 1 (BSF-1) and B cell differentiation factor. It functions to costimulate B cell growth, Ig class switching, T cell growth and differentiation, macrophage activation, regulate mast cell growth, and to costimulate hematopoietic precursor cells.

IL-5, also known as B cell growth factor II (BGF-II), T cell replacing factor, IgA-enhancing factor, and eosinophil colony stimulating factor, is a glycoprotein produced by T lymphocytes and mast cells. This cytokine has the dual functions of a colony stimulating factor, as well as promoting the differentiation of eosinophilic colonies in bone marrow. IL-5 induces specific in vitro antibody production by B cells primed with antigen in vivo. While IL-5 serves as a differentiation factor in vitro, it does not appear to act as a differentiation factor in vivo.

IL-6, also known BSF-II, interferon $\beta 2$, hybridoma/plasmacytoma growth factor, and hepatocyte stimulatory factor, is a glycoprotein produced by both lymphoid and nonlymphoid cells. This cytokine regulates immune responses, acute-phase reactions, and hemopoiesis. IL-6 acts on B cell lines at the mRNA level and induces biosynthesis of secretory-type Ig. In addition to IL-5, IL-6 has also been shown under very restricted conditions to function as a differentiation factor. All other known T cell or macrophage derived factors that have been tested cannot induce activated B cells to secrete Ig in the absence of added growth factors.

IL-10, also known as cytokine synthesis inhibitory factor, is produced by T cells, macrophages, and other cell types. This cytokine inhibits several macrophage functions, including cytokine synthesis and some microbial activities, in addition to enhancing or stimulating mast cells and B cells. IL-10 causes strong proliferation of human B cells activated by anti-CD40 antibodies or cross-linking of the antigen receptor.

In addition to the interleukins, other cytokines have been characterized. Colony stimulating factors (CSFs) are a group of factors primarily concerned with hematopoiesis. They are defined as proteins which stimulate the clonal growth of bone-marrow cells in vitro.

Granulocyte-macrophage colony stimulating factor (GM-CSF) is a glycoprotein growth factor that modulates the growth or differentiation of hemopoietic cells. This growth factor can be produced by a number of different cells under different circumstances, including T cells, macrophages, endothelial cells, stromal cells, fibroblasts, mast cells, and others. The major actions of GM-CSF involve the regulation of survival, differentiation, and proliferative and functional activities in granulocyte-macrophage populations. There are no reports prior to the invention indicating that GM-CSF can stimulate the release of antibody by B cells.

Finally, another class of cytokines that function in the body's immune system is interferons (IFNs). IFNs are major contributors to the first line of antiviral defense by inhibiting virus replication, in addition to exerting many other important effects on cells. IFNs do not act directly to protect cells from infection. Rather, they stimulate production of a protein in neighboring cells that stops the growth of the virus, thus protecting the cells from infection.

IFNs are classified into three groups, alpha, beta, and gamma, based on the cells of origin and method of induction. The production of IFN-$\alpha$ and IFN-$\beta$ is not a specialized cell function, and probably all cells of the organism are capable of producing these IFNS.

In contrast to IFN-$\alpha$ and IFN-$\beta$ synthesis, which can occur in any cell, production of IFN-$\gamma$ is a function of T cells and NK cells. All IFN-$\gamma$ inducers activate T cells either in a polyclonal (mitogens or antibodies) or in a clonally restricted, antigen-specific manner. Human IFN-$\gamma$ promotes proliferation of activated human B cells and, in cultures of human B cells, can act synergistically with IL-2 to enhance immunoglobulin light-chain synthesis.

The brief discussion describing functions of various human immune cells, and the known activities of IL-1, IL-2, IL-3, IL-4, IL-5, IL-6, IL-10, GM-CSF, and IFN-$\gamma$ exemplifies the extreme diversity of the human immune system. Despite this level of knowledge, however, there is no complete understanding of the intricacies of the immune system. Tremendous gaps remain. For example, it is not possible to make general statements about the properties of cytokines, except that they act as intercellular mediators by regulating responses of cells of the immune system. Thus, there remains a need in the art for a greater understanding of the immune system and for the provision of additional and superior methods of treating immune disorders.

SUMMARY OF THE INVENTION

The present invention fulfils a need in the art for new and improved immunotherapies. The novel compositions and methods, employing IL-3, GM-CSF, and IFN-$\gamma$, enable improved and new treatments for immune disorders, as well as adjuvants for current immunotherapies.

This invention is directed to a composition of GM-CSF and IL-3, either alone or in combination, present in an amount effective for the stimulation of antibody release by B cells. Molecularly engineered fragments of GM-CSF or IL-3 that retain GM-CSF or IL-3 activity can also be employed in the invention.

Another object of this invention is a composition of GM-CSF and IL-3, either alone or in combination, along with IFN-γ, all of which are present in amounts effective for the stimulation of antibody release by B cells.

A further object of the invention is a pharmaceutical composition comprising the novel compositions and a pharmaceutically acceptable carrier.

The use of the novel compositions comprising GM-CSF, IL-3, and IFN-γ to stimulate the release of antibody by B cells is also encompassed by the invention. A method of stimulating the release of antibody by B cells can be used to bolster mammalian immune responses to, for example, vaccination under conditions of normal or immunocompromised conditions.

A further object of this invention is the use of the novel compositions as adjuvants for vaccines. For example, many vaccines are currently administered intravenously or intramuscularly to allow a rapid stimulation of immune cells present in the blood system. By combining the novel compositions, either as a fusion protein covalently linked to a carrier molecule, admixed, or any other combination, with a vaccine to be administered, the magnitude of the antibody response can be increased both at the systemic and local levels.

Another object of this invention is neutralization of GM-CSF, IL-3, and IFN-γ under conditions where the production of antibody is pathogenic, such as in autoimmune disorders.

The compositions can also be used to optimize monoclonal antibody production in vitro or in vivo. For example, an animal can be sensitized with antigen and the compositions in vivo. Alternatively, in vitro stimulation or sensitization of lymphocytes to produce antibody can be enhanced in the presence of the novel compositions. This is particularly useful for the production of human monoclonal antibodies.

This invention is also directed to a novel assay system that allows the identification of compositions useful for stimulating antibody release by B cells. This assay system, which mimics in vivo antibody stimulation, comprises dextran-conjugated anti-Ig antibodies and highly purified B cells. The anti-Ig-dextran conjugate effectively and polyclonally activates the B cells via membrane Ig by a mechanism comparable to activation of B cells induced by antigen in vivo.

Other objects and advantages of the present invention will be set forth in part in the description which follows, and in part will be obvious from this description, or may be learned from the practice of this invention. The accompanying drawings and tables, which are incorporated in and constitute a part of this specification, illustrate and, together with this description, serve to explain the principle of the invention.

BRIEF DESCRIPTION OF THE DRAWINGS

To this medium was added a supernatant from a cell culture described in the parent application, RA5-SN, and GM-CSF or IL-3. A control composition was also measured. The RA5-SN supernatant, having both GM-CSF and IL-3, showed significant IgM secretion by B cells as compared to other tested compositions.

FIG. 2: B cells were activated with dextran-conjugated anti-IgD antibodies (3 ng/ml) plus IL-1 (150 U/ml)+IL-2 (150 U/ml) in the presence or absence of varying concentrations of IL-3 or GM-CSF (FIGS. 2a and 2b, respectively). IgM secretion was measured by ELISA 6 days after initiation of culture.

FIG. 6: B cells were activated with dextran-conjugated anti-IgD antibodies (3 ng/ml) plus IL-1 (150 U/ml)+IL-2 (150 U/ml) in the presence or absence of IL-3 (100 U/ml) and/or GM-CSF (100 U/ml). FIGS. 6a and 6b IgM secretion and cellular outgrowth, respectively. Viable cells (those that excluded trypan blue) were enumerated 4 days after initiation of culture using a hemocytometer. IgM concentrations in replicate cultures were measured by ELISA 6 days after initiation of culture. Data is represented as mean +/– standard error of the mean of duplicate cultures.

DESCRIPTION OF PREFERRED EMBODIMENTS

The invention describes compositions of cytokines which individually and in combination lead to 100 fold enhancement in antibody secretion by B cells. The compositions comprise IL-3 and GM-CSF, either alone or in combination, in an amount effective for stimulating the release of antibody by B cells. Also encompassed by the invention are compositions comprising IL-3 and GM-CSF, either alone or in combination, and IFN-γ, all present in amounts effective for stimulating the release of antibody by B cells. More preferably, the compositions additionally comprise CD40 ligand (CD40L) or at least one other cytokine, or a combination thereof. Most preferably, the compositions comprise GM-CSF, IL-3, or a combination thereof, IFN-γ, CD40L, and IL-1+IL-2.

The enhancement in Ig secretion mediated by IL-3 or GM-CSF typically ranges between 10–50 fold, and the combination of IL-3 and GM-CSF induces enhancement of up to 100 fold. Preferably, GM-CSF and IL-3 are present at from about 1 to about 10 U/ml, in vitro. In vivo amounts are scaled up accordingly, as is well known in the art. More preferably, GM-CSF and IL-3 are present at from about 10 up to about 100 U/ml, and in particular, at about 100 U/ml.

IDENTIFICATION OF IL-3, GM-CSF, AND IFN-γ AS B CELL STIMULATORY AGENTS

Prior to the invention, it was not known that GM-CSF or IL-3 act directly on the B cell to stimulate the release of antibody, or that GM-CSF and IL-3 act synergistically and directly on the B cell to stimulate the release of antibody. Moreover, GM-CSF has not been previously implicated in directly regulating mature B cell function. It was also not known that addition of IFN-γ 24 hours after stimulation could by itself stimulate optimal antibody secretion, nor that it could further enhance the activity of IL-3 and GM-CSF, either alone or in combination.

The composition described in parent application Ser. No. 08/150,410 comprised IL-3 and GM-CSF. Early experiments determined that the Ig secretory response of electronically sorted highly purified B cells was significantly lower than B cell enriched populations that contained small numbers of "non-T, non B" cells. Based on these findings, the first application showed that NK cells and/or NK cell-derived cytokines could enhance Ig secretion in anti-Ig-dextran stimulated B cells.

The parent application also disclosed supernatants derived from T cell clones (TH1 or TH2) that enhanced Ig secretion by B cells. Experiments determined that this enhancement was not due to IL-1, IL-2, IL-5, IL-6, or IL-10. Surprisingly, it was discovered that the differentiation-inducing activity was due to the presence of GM-CSF and IL-3. When GM-CSF and IL-3 were added to anti-Ig-dextran stimulated cells, Ig secretion was induced. Conversely, when anti-GM-CSF and/or anti-IL-3 were added, the stimulatory activity of the T cell supernatants was diminished.

It was also found that Ig secretion could be further enhanced by the addition of IL-2, the addition of IFN-γ 24 hours after culture, or the addition of IFN-γ+IL-2. Maximum levels of Ig secretion were induced when IL-2, IL-3, and GM-CSF were added to anti-Ig-dextran stimulated cells at the onset of culture, and IFN-γ was added one day later (24 hr period after stimulation with anti-Ig-dextran). IFN-γ added immediately following B cell activation does not enhance the stimulatory effect, or minimally enhances the stimulatory effect, of IL-3 or GM-CSF. Thus, the timing of the addition of IFN-γ is important for further enhancing the release of antibody by B cells. This discovery has not been reported prior to the invention.

To determine whether the activity of IL-3 or GM-CSF, or IL-3+GM-CSF, could account for the differentiating activity of the TH1 or TH2 derived supernatant, the effect of adding neutralizing quantities of anti-IL-3 or anti-GM-CSF antibody on Ig secretion was analyzed. While each antibody mediated significant suppression of Ig secretion, the combination of anti-IL-3 and anti-GM-CSF induced a greater than 80% suppression of Ig secretion in anti-Ig-dextran stimulated cells in the presence of TH-1 or TH2-derived supernatant.

The findings that IL-3 and GM-CSF can enhance Ig secretion by B cells, and that anti-IL-3+anti IL-GM-CSF can suppress Ig secretion, were completely unexpected. Moreover, it was also surprising that IFN-γ added 24 hours after the onset of culture enhanced the stimulatory effect of IL-3 and GM-CSF. These findings have not been previously reported.

PHARMACEUTICAL COMPOSITIONS

Pharmaceutical compositions are also encompassed by the invention. Such compositions comprise an effective amount of IL-3 and GM-CSF, either alone or in combination, and a pharmaceutically acceptable carrier. Also encompassed by the invention are pharmaceutical compositions comprising an effective amount of IL-3 and GM-CSF, either alone or in combination, and an effective amount of IFN-γ, along with a pharmaceutically acceptable carrier.

Treatment comprises administering the pharmaceutical composition by intravenous, intraperitoneal, intracorporeal injection, intra-articular, intraventricular, intrathecal, intramuscular, subcutaneous, intranasally, intravaginally, orally, or by any other suitable method of administration. The composition may also be given locally, such as by injection to the particular area, either intramuscularly or subcutaneously.

Any pharmaceutically acceptable carrier can be employed for GM-CSF, IL-3, and IFN-γ. Carriers can be sterile liquids, such as water, oils, including petroleum oil, animal oil, vegetable oil, peanut oil, soybean oil, mineral oil, sesame oil, and the like. With intravenous administration, water is a preferred carrier. Saline solutions, aqueous dextrose, and glycerol solutions can also be employed as liquid carriers, particularly for injectable solutions. Suitable pharmaceutical carriers are described in *Remington's Pharmaceutical Sciences*, 18th Edition (A. Gennaro, ed., Mack Pub., Easton, Pa., 1990), incorporated by reference.

Vaccine adjuvants comprising the compositions

This invention also encompasses vaccine adjuvants comprising the compositions of the invention. Many vaccines are currently administered intravenously or intramuscularly to allow a rapid stimulation of immune cells present in the blood system. By combining the novel compositions with a drug to be administered, the magnitude of the antibody response is increased, both locally and systemically.

In the in vitro assay, the anti-IgM or anti-IgD antibody when presented in a multivalent form, such as dextran, acts efficiently to activate all B cells. This high level of activation, coupled with the use of highly purified B cells, allows the identification of compounds that stimulate the release of antibody by B cells. However, this response is not desired in vivo. In a patient, the goal is to activate only a small number of B cells having receptors specific for the antigen. The specific antigen of the vaccine acts to cross-link specific B cell receptors. In contrast, the in vitro model employing anti-Ig-dextran acts to cross-link all antigen receptors.

Preferably, when used as a vaccine adjuvant, the compositions of the invention are conjugated to a multivalent carrier molecule, such as dextran or a capsular polysaccharide. of a bacteria. Pneumococci, streptococci, and meningococci capsular polysaccharides are preferred. GM-CSF, IL-3, molecularly engineered fragments of GM-CSF or IL-3 that retain. GM-CSF or IL-3 activity, or a combination thereof, can be independently conjugated to the multivalent carrier. Alternatively, GM-CSF and IL-3 can be fused together or fused to another protein to form a fusion protein, which can also be bound to the multivalent carrier. Other vaccine variations will be apparent to one of skill in the art.

This application encompasses the use of anti-cytokine-cytokine complexes which allow for the slow but prolonged delivery of the cytokine. The complexes can be administered as a mixture with the antigen of a vaccine, or the complexes can be bound to the antigen of a vaccine.

In still another embodiment, the vaccine adjuvant can comprise CD40L, one or more cytokines other than GM-CSF, IL-3, or IFN-γ, or a combination thereof. CD40L and the one or more cytokines can also be bound to the multivalent carrier.

Compositions used in a conjugate vaccine

To form a conjugate vaccine, the antigen of the vaccine and the compositions of the invention can be covalently conjugated to a multivalent carrier molecule, such as dextran or a capsular polysaccharide of a bacteria. Pneumococci, streptococci, and meningococci capsular polysaccharides are preferred.

The antigen is a peptide or protein specific for the disease to be vaccinated against.

To further optimize the humoral immune response upon administration of the vaccine, CD40 or at least one other cytokine, or a combination thereof, can be conjugated to the multivalent carrier.

Table III shows exemplary vaccines employing the compositions of the invention. As noted in the Table, several of the vaccines are conjugate vaccines. Methods of conjugation are well known to those of ordinary skill in the art, and include the heteroligation techniques of Brunswick et al., *J. Immunol.*, 140:3364 (1988); Wong, S. S., *Chemistry of Protein Conjugates and Crosslinking*, CRC Press, Boston (1991); and Brenkeley et al., "Brief Survey of Methods for Preparing Protein Conjugates With Dyes, Haptens and Cross-Linking Agents," *Bioconjugate Chemistry*, 3, No. 1 (Jan. 1992), specifically incorporated by reference.

METHODS OF USING THE COMPOSITIONS

A further object of this invention is the use of the compositions comprising IL-3 and GM-CSF, either alone or in combination, and compositions comprising IL-3 and GM-CSF, either alone or in combination, along with IFN-γ, to stimulate the release of antibody by B cells.

Suitable hosts for treatment include any suitable mammal. Preferred hosts are humans, including neonates, adults, and immunodeficient patients.

The compositions can be administered employing any suitable administration method. Preferable methods of administering the compositions include subcutaneously, intravenously, nasally, mucosal routes, orally, intramuscularly, or a combination thereof.

The dosage of the compounds employed varies depending upon age, individual differences, symptoms, mode of administration, etc., and can be readily determined by one of skill in the art. Exemplary dosages of GM-CSF and IL-3 are given in J. Nemunaitis, "Granulocyte-macrophage-colony-stimulating factor: a review from preclinical development to clinical application," *Transfusion*, 33, 70–83 (1993); Lieschke et al., "Granulocyte Colony-Stimulating Factor and Granulocyte-Macrophage Colony-Stimulating Factor (First of Two Parts)," *The N. Eng. J. of Med.*, 327, 28–35 (1992); Lieschke et al., "Granulocyte Colony-Stimulating Factor and Granulocyte-Macrophage Colony-Stimulating Factor (Second of Two Parts)," *The N. Eng. J. of Med.*, 327, 99–106 (1992); Schulz et al., "Adjuvant Therapy with Recombinant Interleukin-3 and Granulocyte-Macrophage Colony-Stimulating Factor," *Pharmac. Ther.*, 52, 85–94 (1992); Hoelzer et al., "Interleukin 3 Alone and in Combination with GM-CSF in the Treatment of Patients with Neoplastic Disease," *Seminars in Hematology*, 28, suppl. 2 (April), 17–24 (1991).

NEUTRALIZING METHODS OF USING THE COMPOSITIONS

Another object of this invention is methods of neutralizing the activity of GM-CSF, IL-3, and IFN-γ under conditions where the production of antibody is pathogenic, such as in autoimmune disorders, such as lupus, systemic lupus erythemato'sus (SLE), idiopathic thrombocytopenic purpura (ITP), vasculitis, Graves' disease, allergic reactions, etc.

For the construction of a neutralizing vaccine, an antibody against the cytokine is made. Those of ordinary skill in the art are familiar with the well established methods of obtaining specific antibody. The antibody is then administered to a patient. The antibody can be bound to a carrier to increase the half-life of the antibody.

METHODS OF USING THE COMPOSITIONS TO OPTIMIZE MONOCLONAL ANTIBODY PRODUCTION

The compositions can also be used to optimize monoclonal antibody production in vitro or in vivo. For example, an animal can be sensitized by injecting a solution containing the antigen of interest and the compositions in vivo. Because the compositions stimulate the release of antibody by B cells, the administration of the compositions in conjunction with the specific antigen will optimize the production of antibody against the specific antigen.

Those of ordinary skill in the art would be familiar with techniques for such immunization, as well as the dosages of the antigen and compositions needed to elicit the antibody and to stimulate its release in light of the teachings in this specification.

Alternatively, in vitro stimulation or sensitization of lymphocytes to produce antibody can be enhanced in the presence of the novel compositions. The teachings for such stimulation and sensitization are well within the routine skill of those in the art, as is the determination of the appropriate amounts of antigen and compositions to apply in light of the teachings in this specification. This method is particularly useful for the production of human monoclonal antibodies.

ASSAY SYSTEM FOR IDENTIFYING COMPOSITIONS USEFUL FOR STIMULATING THE RELEASE OF ANTIBODY BY B CELLS

A further embodiment of the invention is the development of a novel in vitro assay system that mimics in vivo antibody stimulation. The assay system allows the identification of compositions that stimulate the release of antibodies by B cells.

Because resting B cells do not release antibody, they must first be activated before antibody release can be measured. In the present invention, anti-IgM or anti-IgD antibody is covalently conjugated to high molecular weight dextran (i.e., MW=$2.0 \times 10^6$) to create a multivalent antigen on a polysaccharide carrier, as set forth in Snapper et al., "Comparative In Vitro Analysis of Proliferation, Ig Secretion, and Ig Class Switching by Murine Marginal Zone and Follicular B Cells," *J. of Immunology*, 150, 2737–2745 (1993), specifically incorporated by reference. This procedure converts the bivalent anti-Ig molecule into an extremely stimulatory multivalent conjugate which can induce persistent and repetitive signaling via B cell membrane Ig, even at picomolar concentrations. The anti-Ig-dextran conjugate stimulates high levels of B cell proliferation at concentrations as low as 1 pg/ml, a concentration 10,000 fold lower than that stimulated by unconjugated anti-Ig. The activation of B cells occurs irrespective of antigen specificity. Anti-Ig-dextran does not stimulate the release of antibody by resting B cells in the absence of cytokines. With the addition of a cytokine that stimulates the release of antibody by B cells, high levels of Ig secretion are observed.

Previously, it was known that activation of B cells through the antigen receptor can be optimally achieved using an anti-immunoglobulin (Ig) antibody conjugated to a large molecular weight polysaccharide, e.g., dextran. However, it was not possible to screen for compositions that stimulate the release of antibody by B cells because, previously, the B cells employed in the assays were not highly purified. Contaminating cells in the B cell supernatant often secreted sufficient amounts of cytokines that could stimulate the release of antibody by B cells. Therefore, it was not possible to determine whether the stimulatory effect of a tested composition was due to the added composition or to a contaminant.

In contrast, the present invention employs highly purified B cells in the assay system. Preferably, the B cells are electronically sorted to produce highly purified B cells. With the use of highly purified B cells, it is possible to measure the stimulatory effects of substances on the release of antibody by B cells activated through multivalent mIg cross-linking. This system was not described prior to the invention. In fact, it was not possible to test compositions for the sole characteristic of stimulatory activity on the release of antibody by B cells prior to the discovery of this assay system.

The unexpected effect of the present invention is demonstrated in the following experiments and is depicted in FIGS. 1–6.

Having generally described the invention, a more complete understanding can be obtained by reference to specific examples, which are provided herein for purposes of illustration only and are not intended to be limiting.

Example 1

This example shows that the B cell antibody stimulatory activity of the cell supernatant reported in the parent application was not due to one known cytokine.

Materials and Methods: Female DBA/2 mice were obtained from the National Cancer Institute (Frederick, Md.) and were used at 7–10 weeks of age. Culture medium used was RPMI 1640 (Biofluids, Rockville, Md.) supplemented with 10% fetal bovine serum (Sigma, St. Louis, Mo.), L-glutamine (2 mM), 2-mercaptoethanol (0.05 mM), penicillin (50 µg/ml) and streptomycin (50 µg/ml).

Dextran-conjugated anti-IgD antibody was prepared by conjugation of $H\delta^a/1$ (monoclonal mouse IgG2b (b allotype)) anti-mouse IgD (a allotype) to a high molecular weight dextran ($2\times10^6$ MW). Approximately 9 dextran-conjugated anti-IgD antibodies were conjugated to each dextran molecule. FITC-anti-CD3ε mAb (2C11) was purchased from Pharmingen (San Diego, Calif.).

PE-labeled affinity-purified polyclonal goat anti-mouse IgM antibody was purchased from Southern Biotechnology Associates (Birmingham, Ala.). Murine recombinant IL-1 and IL-2 were kind gifts from Dr. Stephanie Vogel (USUHS, Bethesda, Md.) and Dr. Maurice Gately (Hoffman-La Roche, Nutley, N.J.), respectively. Recombinant murine IL-3 and GM-CSF were purchased from Pharmingen. Polyclonal goat anti-mouse IL-3 and GM-CSF antisera were both obtained from R & D Systems (Minneapolis, Minn.).

Functional assays were carried out in 96-well flat-bottom Costar plates (Costar, Cambridge, Mass.). Cultured cells were incubated at $1\times10^5$ cells/ml in a total volume of 200 µL at 37° C. in a humidified atmosphere containing 6% $CO_2$.

Polyclonal IgM concentrations were measured by ELISA. Quantitation was achieved by comparison with IgM standard curves employed in every assay.

Preparation and culture of B cells: Enriched populations of B cells were obtained from spleen cells. T cells were eliminated by treatment with rat anti-Thy-1, anti-CD4, and anti-CD8 monoclonal antibodies, followed by monoclonal mouse anti-rat Igk and complement. Cells were fractionated on the basis of their density over discontinuous PERCOLL gradients (polyvinylpyrrolidone-coated silica colloid) (Pharmacia, Piscataway, N.J.) consisting of 70, 65, 60, and 50% Percoll solutions (with densities of 1.086, 1.081, 1.074, and 1.062 g/ml, respectively). The high density (small, resting) cells were collected from the 70 to 65% interface and consisted of ~90% B cells. Highly purified B cells were then obtained by electronic cell sorting of membrane (m)IgM+CD3- cells on an EPICS ELITE cytometer (Coulter Corp., Hialeah, Fla.) after staining with FITC-anti-CD3ε+ PE-anti-IgM antibodies. Sorted cells were immediately re-analyzed and found to be consistently >99% B cells. These cells were used in all experiments.

TH1 mouse cell lines were cloned and used for the experiments. As described in the parent application, a composition which stimulated the release of antibody by B cells was isolated. To determine the identity of the components of the composition, the activity of all known cytokines was systematically suppressed by adding monoclonal antibodies specific for IL-1, IL-2, IL-3, etc., to the composition, and then measuring activity.

Because the composition comprised two independent B cell antibody release stimulators, IL-3 and GM-CSF, experiments suppressing each known cytokine one by one did not result in completely suppressing the measured activity.

Example 2

This example determines the relative stimulatory effects of a supernatant of a T cell culture identified in the parent application, GM-CSF, and IL-3.

IgM secretion (ng/ml) by B cells in various mediums was measured. Culture mediums are listed along the left side FIG. 1. Culture mediums were anti-IgD-dextran and IL-1+ IL-2; anti-IgD-dextran and IL-4; soluble CD40 ligand and IL-1 +IL-2; soluble CD40 ligand and IL-4, membrane CD40 ligand; membrane CD40 ligand and IL-1 +IL-2; and membrane CD40 and IL-4. The compositions tested were a supernatant of a cell culture described in the parent application, RA5-SN, GM-CSF, and IL-3. A control composition was also tested for each medium.

Figure 1:
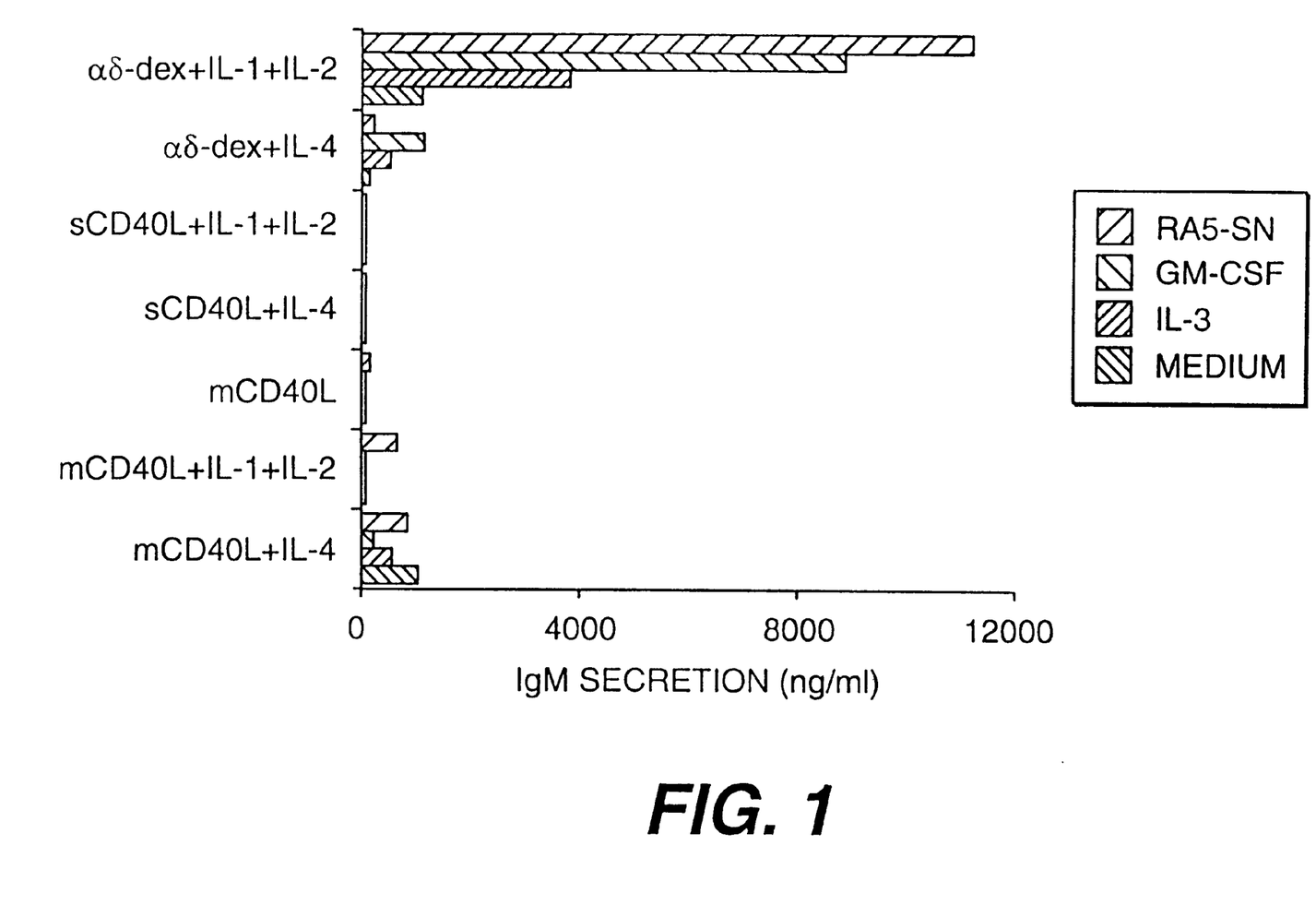
FIG. 1: IgM secretion (ng/ml) by B cells in various mediums was measured. Culture mediums are listed along the left side of the chart. The compositions tested showed the highest IgM secretion in medium comprising dextran-conjugated anti-IgD antibody, IL-1, and IL-2.

As set forth in FIG. 1, compositions tested showed the highest IgM secretion in medium comprising dextran-conjugated anti-IgD antibody, IL-1, and IL-2. The RAS-SN supernatant, having both GM-CSF and IL-3, showed significant IgM secretion by B cells as compared to other tested compositions.

Example 3

This example shows that IL-3 and GM-CSF stimulate Ig secretion by activated B cells.

B cells were activated with dextran-conjugated anti-IgD antibodies (3 ng/ml) plus IL-1 (150 U/ml)+IL-2 (150 U/ml) in the presence or absence of varying concentrations of IL-3 or GM-CSF. IgM secretion was measured by ELISA 6 days after initiation of culture.

Electronically sort-purified resting B cells proliferated but failed to secrete Ig in response to activation by dextran-conjugated anti-IgD antibody or dextran-conjugated anti-IgD antibody plus IL-1 +IL-2. As reported in the parent application, supernatants obtained from anti-CD3-activated CD4+TH1 and TH2 clones induce strong Ig secretory responses by B cells stimulated with dextran-conjugated anti-IgD antibody plus IL-1+IL-2. This stimulation is IL-4 and IL-5-independent.

Because TH1 and TH2 clones share the capacity to secrete IL-3, GM-CSF, and TNF-α upon activation, these cytokines were tested for their ability to induce Ig secretion.

Figure 2A:
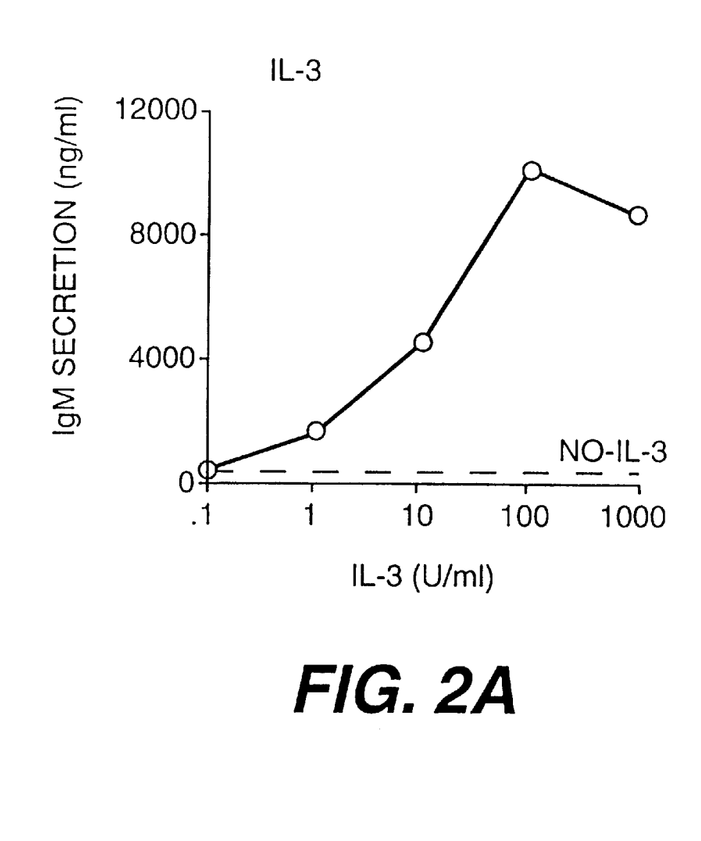
Figure 2B:
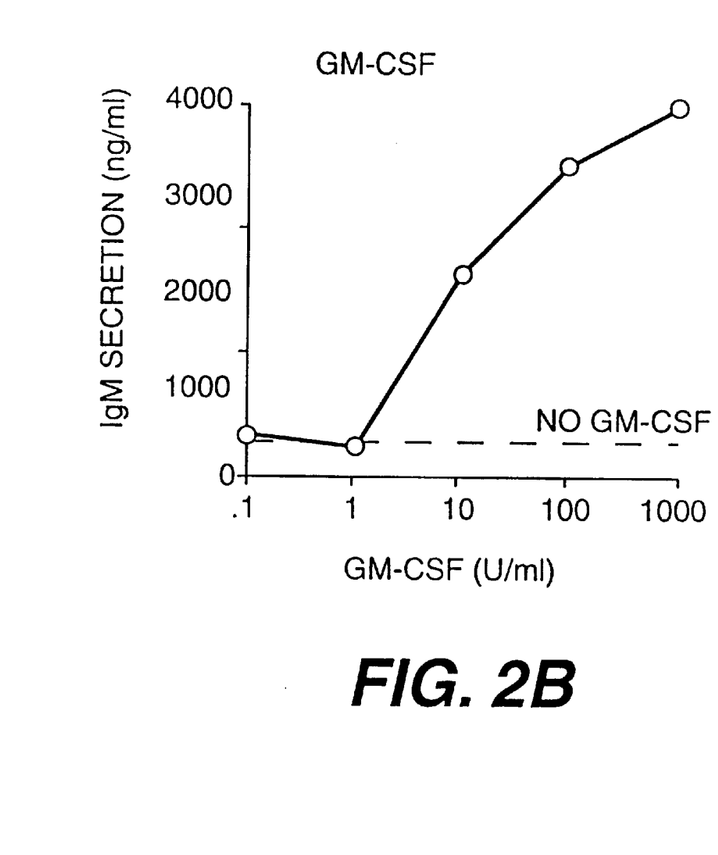

Cytokines were titered in log increments from 0.1 to 1000 U/ml final concentration. TNF-A had no effect on Ig synthesis. In contrast, IL-3 and GM-CSF stimulated significant enhancements in Ig secretion over that observed with dextran-conjugated anti-IgD antibody plus IL-1+IL-2 alone (FIG. 2a and 2b). Both IL-3 and GM-CSF stimulated optimal Ig secretory responses at 100 U/ml, producing a 19- and 9-fold enhancement, respectively. Significant, though lower, levels of induction of Ig synthesis in response to IL-3 or GM-CSF were still observed at 1–10 U/ml.

Figure 3:
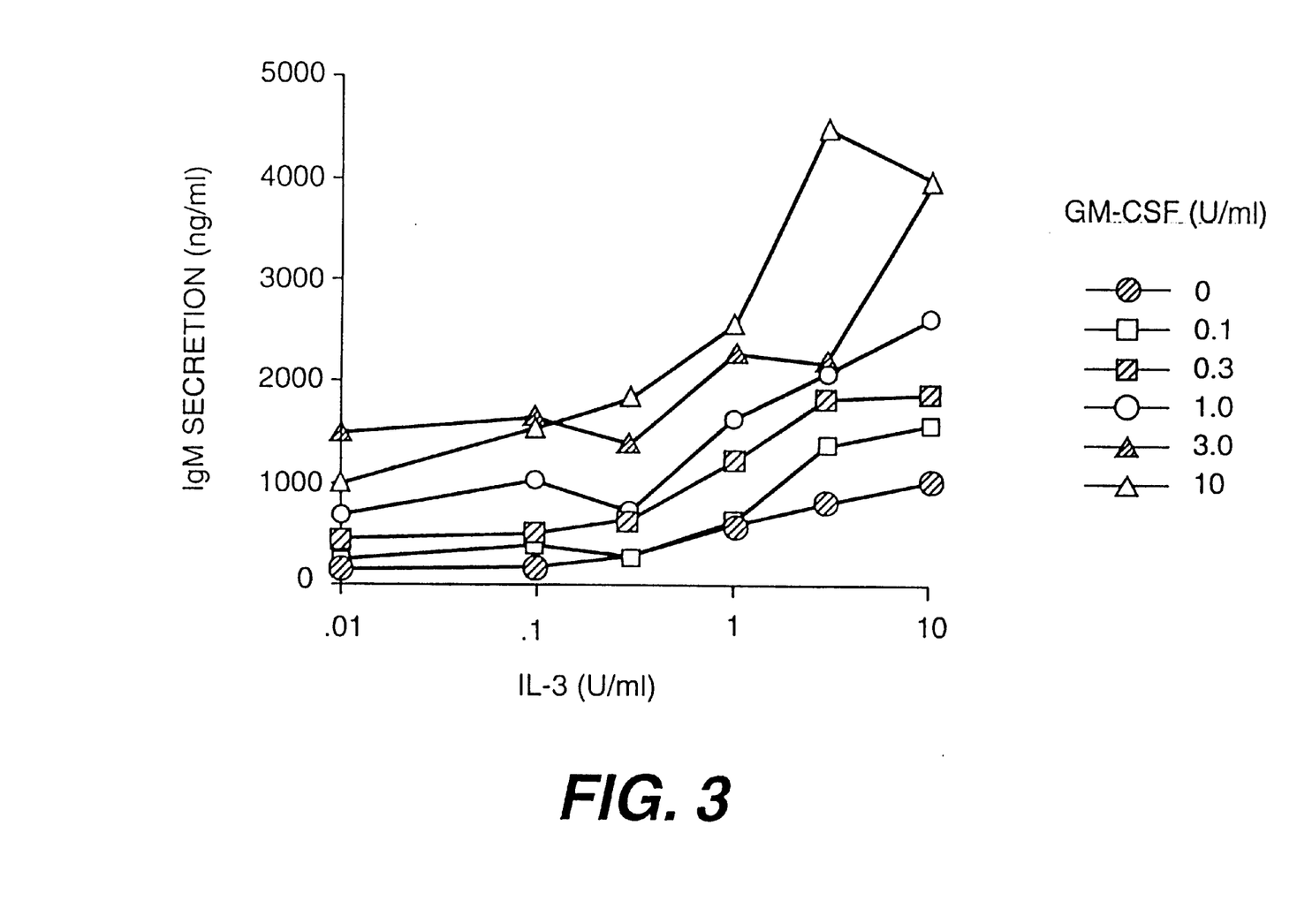
FIG. 3: IgM secretion (ng/ml) by activated B cells was measured with the addition of varying concentrations of GM-CSF and IL-3. Maximum IgM secretion of about 4650 ng/ml was obtained with the addition of GM-CSF at 10 U/ml and IL-3 at about 3 U/ml.

In multiple experiments the degree of enhancement in Ig secretion mediated by IL-3 and GM-CSF typically ranged between 10–50 fold (FIG. 3). No significant differences were observed between IL-3 and GM-CSF for either dose response or optimal level of induction of Ig secretion.

Example 4

This example demonstrates that anti-IL-3 and anti-GM-CSF antibodies specifically inhibit the induction of Ig secretion in response to IL-3 and GM-CSF, respectively.

Figure 4:
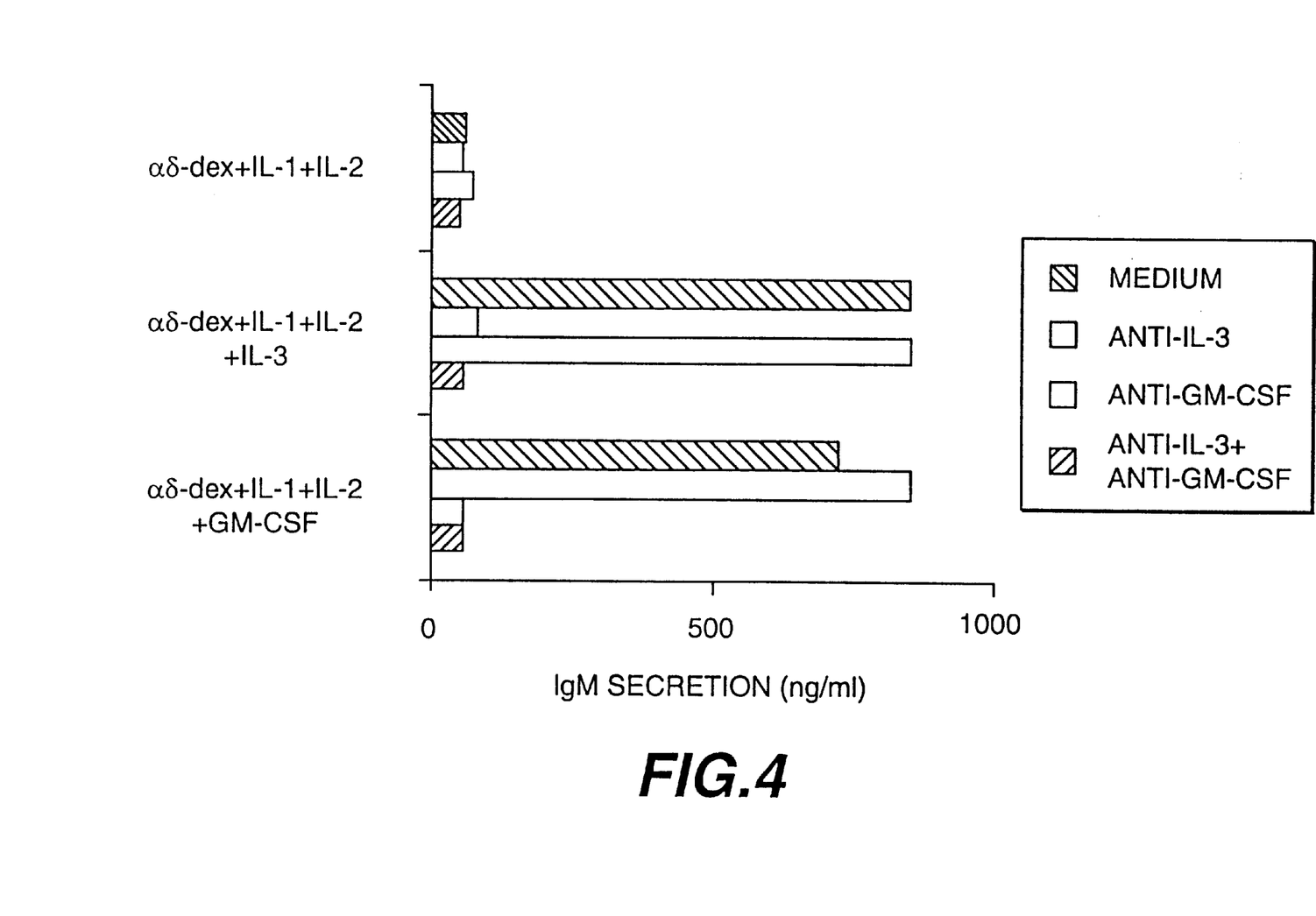
FIG. 4: B cells were activated with dextran-conjugated anti-IgD antibodies (3 ng/ml) plus IL-1 (150 U/ml)+IL-2 (150 U/ml) in the presence or absence of IL-3 (10 U/ml) or GM-CSF (10 U/ml). In addition, anti-IL-3 (10 μg/ml) and/or anti-GM-CSF (10 μg/ml) antibodies were added. A control with no added anti-IL-3 or anti-GM-CSF was also prepared. IgM concentrations were measured by ELISA 6 days after initiation of culture.

B cells were activated with dextran-conjugated anti-IgD antibodies (3 ng/ml) plus IL-1 (150 U/ml)+IL-2 (150 U/ml) in the presence or absence of IL-3 (10 U/ml) or GM-CSF (10 U/ml). In addition, anti-IL-3 (10 μg/ml) and/or anti-GM-CSF (10 μg/ml) antibodies were added. A control with no added anti-IL-3 or anti-GM-CSF was also prepared. IgM concentrations were measured by ELISA 6 days after initiation of culture.

Neutralizing anti-IL-3 and anti-GM-CSF antibodies specifically and completely inhibited the respective Ig-inducing activities of IL-3 and GM-CSF (FIG. 4). These antibodies, either alone or in combination, had no effect on the Ig secretory response to dextran-conjugated anti-IgD antibody+IL-5 activation (data not shown). Results also demonstrated that the combination of anti-IL-3 and anti-GM-CSF antibodies could significantly reduce the IL-4+IL-5-independent Ig-inducing activities of supernatants from either a CD4+ TH1 or TH2 clone. It was also demonstrated that IL-3 and GM-CSF could not induce Ig secretion by B cells activated through the CD40-mediated signalling pathway.

Example 5

This example demonstrates that IL-3 and GM-CSF induce Ig secretion by B cells activated with dextran-conjugated, but not unconjugated, anti-IgD antibodies. This example also shows that IL-3 and GM-CSF act synergistically with IL-1 +IL-2.

Multivalent, but not bivalent, mIg cross-linkage costimulates cytokine-mediated Ig secretion and class switching. In this example, dextran-conjugated anti-IgD (H$\delta^a$/1 mAb) was compared with unconjugated anti-IgD (H$\delta^a$/1 mAb) for costimulation of Ig secretion in response to IL-3 or GM-CSF.

B cells were first cultured with AF7 supernatant, αIL-4, and αIL-5. For AF7 supernatant, KLH-specific, Ia$^b$-restricted, CD4+ T cell clone, derived from C57BL/6 mice, was established and maintained by standard methodologies. AF7 is a TH2 clone on the basis of its production of IL-4 and lack of production of IL-2 and IFN-γ.

Cytokine-containing supernatant was obtained from cultures of AF7 cells in the following manner: Tissue culture wells were incubated with anti-CD3 mAb (2C11) at 10 μg/ml in PBS for 3 hr at 37° C. and then washed 3× in fresh PBS. AF7 cells, which were allowed to return to their resting state, 7 days after stimulation with antigen, APCs, and IL-2, were added to anti-CD3-coated plates at 1×10$^6$ cells/ml for various times, upon which cell-free supernatants were obtained and either stored at −20° C. or 4° C. In the latter case, supernatant was used in cellular assays within 1–2 weeks of having been harvested.

Figure 5:
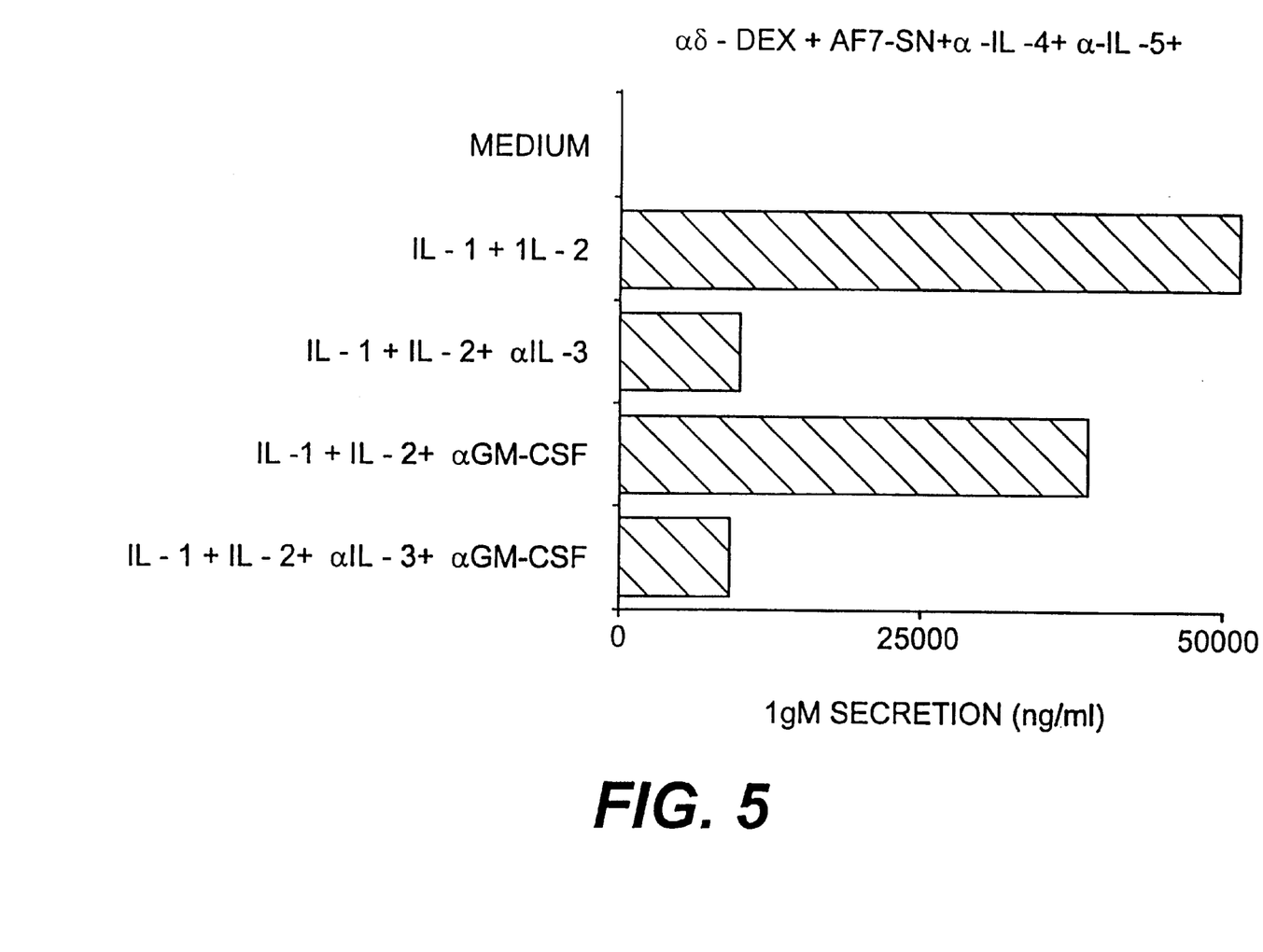
FIG. 5: IgM secretion (ng/ml) by activated B cells was measured for dextran-conjugated anti-IgD antibody-activated B cells in AF7 supernatant. IgM secretion was measured in various mediums comprising two or more of the following: IL-1, IL-2, αIL-3, and αGM-CSF.

B cells were then cultured with dextran conjugated (H$\delta^a$/1-dex, 3 ng/ml) or unconjugated (H$\delta^a$/1, 30 μg/ml) anti-IgD antibodies in the presence or absence of IL-1 (150 U/ml)+IL-2 (150 U/ml). A control composition did not contain conjugated or unconjugated dextran. IL-3 (100 ml) and/or GM-CSF (100 U/ml) were added, and control compositions with no addition of IL-3 or GM-CSF were prepared (FIG. 5). IgM concentrations were measured by ELISA 6 days after initiation of culture.

In contrast to conjugated dextran (H$\delta^a$/1-dex), unconjugated dextran (H$\delta^a$/1) was ineffective as a costimulator of Ig secretion in the presence of IL-3 or GM-CSF (Table 1). These results were obtained despite the ability of unconjugated dextran to induce early B cell activation events, such as increases in cell size and MHC class II induction. IL-3 or GM-CSF alone were unable to induce resting B cells to secrete detectable Ig (Table 1). However, addition of IL-3 and GM-CSF to cultures of dextran-conjugated anti-IgD antibody-activated cells, in the absence of exogenous IL-1 +IL-2, led to 7.4- and 5.4-fold inductions, respectively, of Ig secretion relative to stimulation by dextran-conjugated anti-IgD antibody alone. The addition of IL-1 +IL-2 to cells activated with dextran-conjugated anti-IgD antibody alone did not further increase Ig secretion.

The combination of IL-3 or GM-CSF with IL-1+IL-2 led to 48-fold and 75-fold enhancements in Ig secretion relative to that observed for B cell cultures activated with dextran-conjugated anti-IgD antibody plus IL-1+IL-2 alone. Thus, IL-1+IL-2 is strongly synergistic with IL-3 or GM-CSF for induction of Ig secretion by dextran-conjugated anti-IgD antibody-activated resting B cells.

TABLE I

| Medium | Level of Stimulation |
| --- | --- |
| H$\delta^a$/1-dex | 65 |
| IL-3 | <24 |
| GM-CSF | <24 |
| H$\delta^a$/1-dex + IL-3 | 480 |
| H$\delta^a$/1-dex + GM-CSF | 350 |
| H$\delta^a$/1-dex + IL-1 + IL-2 | 57 |
| H$\delta^a$/1-dex + IL-1 + IL-2 + IL-3 | 2750 |
| H$\delta^a$/1-dex + IL-1 + IL-2 + GM-CSF | 4250 |
| H$\delta^a$/-1 | <24 |
| H$\delta^a$/-1 + IL-1 + IL-2 | <24 |

TABLE I-continued

| Medium | Level of Stimulation |
|---|---|
| Hδ$^a$/-1 + IL-1 + IL-2 + IL-3 | <24 |
| Hδ$^a$/-1 + IL-1 + IL-2 + GM-CSF | <24 |

Example 6

This example demonstrates that both IL-3 and GM-CSF act primarily through stimulation of B cell differentiation to Ig secretion.

To determine the mechanism by which IL-3 and GM-CSF enhance Ig secretion, the effects of IL-3 and GM-CSF on cell outgrowth as compared to Ig secretion were determined.

B cells were activated with dextran-conjugated anti-IgD antibodies (3 ng/ml) plus IL-1 (150 U/ml)+IL-2 (150 U/ml) in the presence or absence of IL-3 (100 U/ml) and/or GM-CSF (100 U/ml). Viable cells (those that excluded trypan blue) were enumerated 4 days after initiation of culture (FIG. 6a) using a hemocytometer (FIG. 6b). IgM concentrations in replicate cultures were measured by ELISA 6 days after initiation of culture. Data is represented as mean +/− standard error of the mean of duplicate cultures.

Figure 6A:
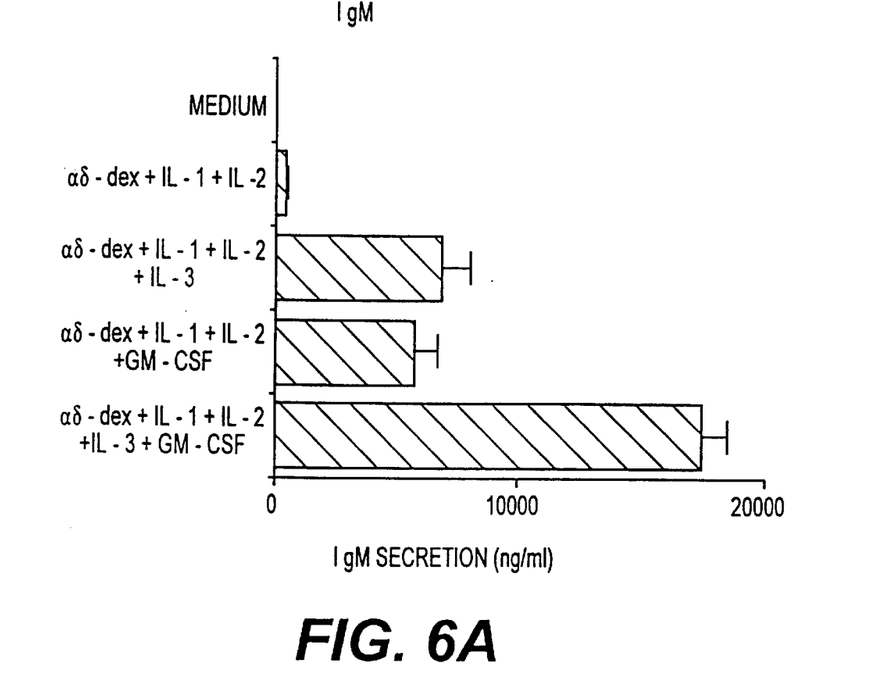
Figure 6B:
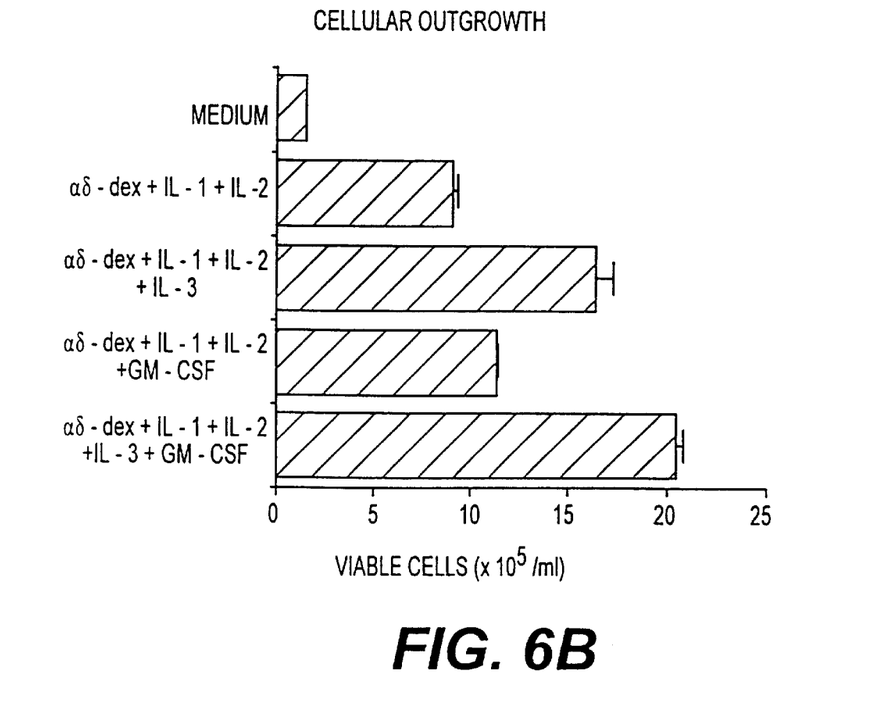

IL-3 stimulated a significant but less than 2-fold enhancement in viable cell outgrowth, whereas GM-CSF had no significant effect on the degree of cell expansion (FIGS. 6a and 6b). Studies assessing DNA synthesis on the basis of $^3$H-thymidine incorporation are consistent with these observations.

The induction of Ig secretion of replicate cultures in response to IL-3 and GM-CSF was 13.8-fold and 13.6-fold, respectively. These results indicate that the primary effect of IL-3 and GM-CSF is to stimulate a strong increase in the average amount of Ig secreted per cell, and not enhancement in the total of number of cells present in culture. Thus, the data strongly suggest that IL-3 and GM-CSF are differentiation factors for resting B cells activated through multivalent antigen receptor cross-linking. The combined action of IL-3 and GM-CSF, utilizing optimal doses of each cytokine, consistently led to greater than additive Ig secretory responses (FIG. 6a). These data indicate that IL-3 and GM-CSF act synergistically. A similar degree of synergism was observed with the combined use of IL-3 and GM-CSF on cells activated with dextran-conjugated anti-IgD antibody in the absence of IL-1+IL-2 (data not shown).

Example 7

This example demonstrates the stimulatory effect on antibody secretion of B cells when CD40L is added to the B cell composition.

B cells were activated with dextran-conjugated anti-IgD antibodies (3 ng/ml or 0.3 ng/ml) plus IL-1 (150 U/ml)+IL-2 (150 U/ml). IgM concentrations in replicate cultures were measured by ELISA for a control composition, for a composition with IL-3+GM-CSF, and for a composition with IL-3+GM-CSF+CD40 ligand (CD40L) (Table II). IL-3 and GM-CSF were present at 100 U/ml. CD40L was in the form of a recombinant soluble CD8–CD40 ligand fusion protein which was added at a final concentration of 10 μg/ml. The fusion protein was a kind gift of Dr. M. Kehry, Boehringer Ingelheim Pharmaceuticals, Inc., Ridgefield, Conn.

TABLE II

| | IgM Secretion (ng/ml) | | |
|---|---|---|---|
| IL-1 + IL-2 | Medium | IL-3 + GM-CSF | IL-3 + GM-CSF + CD40L |
| + medium | <12 | <12 | 115 |
| + anti-IgD-dex (3 ng/ml) | 1,060 | 21,250 | 61,250 |
| + anti-IgD-dex (0.3 ng/ml) | 37 | 3,575 | 42,125 |

The most significant results (61,250 ng/ml) were obtained with anti-IgD-dex at 3 ng/ml and the composition consisting of IL-3+GM-CSF+CD40L. However, even at low levels of the multivalent activator (anti-IgD-dex at 0.3 ng/ml), significant IgM secretion was obtained (42,125 ng/ml). Thus, even at low levels of conjugate, extremely potent antibody release responses can be obtained by including CD40L on a carrier.

Example 8

This example demonstrates the stimulatory effect on antibody secretion of B cells when IFN-γ is added 24 hours after stimulation of the B cells.

Figure 7:
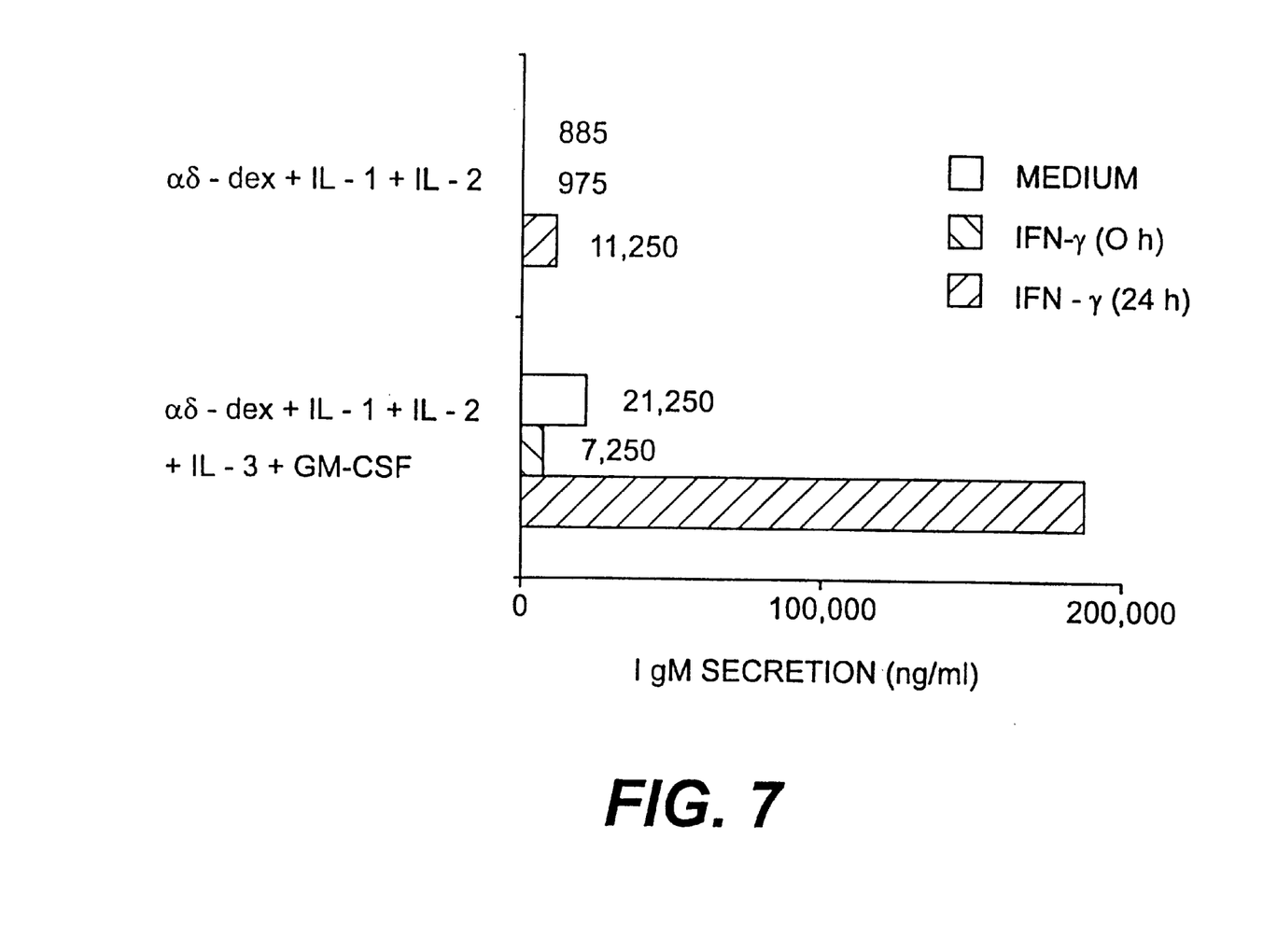
FIG. 7: B cells were activated with dextran-conjugated anti-IgD antibodies (3 ng/ml) plus IL-1 (150 U/ml)+IL-2 (150 U/ml) in the presence or absence of IL-3 (100 U/ml)+ GM-CSF (100 U/ml). IgM concentrations in replicate cultures were measured by ELISA for a control composition, a composition to which IFN-γ was added at 0 h, and for a composition to which IFN-γ was added at 24 h. Data is represented as mean +/– standard error of the mean of duplicate cultures.

B cells were activated with dextran-conjugated anti-IgD antibodies (3 ng/ml) plus IL-1 (150 U/ml)+IL-2 (150 U/ml) in the presence or absence of IL-3 (100 U/ml)+GM-CSF (100 U/ml). IgM concentrations in replicate cultures were measured by ELISA for a control composition, a composition to which IFN-γ was added at 0 h, and for a composition to which IFN-γ was added at 24 h. Data is represented as mean +/− standard error of the mean of duplicate cultures (FIG. 7).

The composition consisting of anti-IgD-dex-activated B cells and IL-1+IL-2 showed minimal IgM secretion with no added INF-γ (885 ng/ml) and minimal secretion with IFN-γ added at 0 hours (975 ng/ml). When IFN-γ was added 24 hours after stimulation of the B cells, antibody secretion jumped to 11,250 ng/ml.

Even more significant results were obtained with a composition consisting of anti-IgD-dex-activated B cells, IL-1+IL-2, and IL-3+GM-CSF. In medium without IFN-γ, antibody secretion was measured at 21,250 ng/ml. Surprisingly, the addition of IFN-γ at 0 hours suppressed antibody secretion to 7,250 ng/ml. However, with the addition of IFN-γ 24 hours after stimulation of the B cells, a synergistic reaction occurred, producing antibody secretion of almost 200,000 ng/ml.

Example 9

This example provides exemplary vaccines and vaccine adjuvants employing the compositions of the invention.

Table III shows exemplary vaccines employing the compositions of the invention. As noted in the Table, several of the vaccines are conjugate vaccines. Methods of conjugation are well known to those of ordinary skill in the art, and include the heteroligation techniques of Brunswick et al., *J. Immunol.*, 140:3364 (1988); Wong, S. S., *Chemistry of Protein Conjugates and Crosslinking*, CRC Press, Boston (1991); and Brenkeley et al., "Brief Survey of Methods for Preparing Protein Conjugates With Dyes, Haptens and Cross-Linking Agents," *Bioconiugate Chemistry*, 3, No. 1 (Jan. 1992), specifically incorporated by reference.

The multivalent carrier replaces the multivalent conjugate (i.e., anti-IgD-dex) employed in vitro. Such a carrier can be, for example, a polysaccharide such as dextran, or a capsular polysaccharide from a bacteria, such as pneumococci, streptococci, or meningococci. The polysaccharide may or may not be medically relevant depending on the use envisioned for the vaccine.

The cytokine can be GM-CSF, IL-3, IFN-γ, or a combination thereof.

This example is not intended to be limiting, and other types of vaccines will be apparent to those skilled in the art from consideration of the specification and practice of the invention.

TABLE III

Vaccine Structure and Components 1. cytokine* + antigen (admixed); coadministration in aqueous solution, slow release particles, adjuvants, etc.
2. cytokine + antigen + multivalent carrier; the cytokine, antigen, or both can be directly conjugated to the carrier, i.e.:

```
    cytokine           cytokine              antigen
    |  antigen            |                    |
    |    |      ; or      |   + antigen; or    |   + cytokine
    multivalent
    carrier
```

3. cytokine-antigen; direct conjugation via covalent bonding
4. cytokine-antigen (covalent bonding) bound to a multivalent carrier, i.e.:

```
    antigen
    |
    cytokine
    |
    multivalent carrier
```

5. cytokine-antigen (fusion protein)
6. cytokine-antigen (fusion protein) bound to a multivalent carrier
7. peptide-cytokine (fusion protein) + antigen
8. peptide-cytokine (fusion protein) + antigen, with the fusion protein, antigen, or both bound to a multivalent carrier
9. cytokine-multivalent carrier, i.e.:

```
                        IL-3
                         |
    GM-CSF  IL-3        GM-CSF
    |        |    ; or    |
    multivalent         multivalent
    carrier              carrier
```

10. antibody complex (i.e., IL-3 + anti-IL-3) + antigen
11. antibody complex (i.e., IL-3 + anti-IL-3) + antigen + multivalent carrier (the cytokine, antigen, or both can be conjugated to the carrier)
12. anti-cytokine antibody; this is a neutralizing vaccine
13. anti-cytokine antibody + multivalent carrier; this is a neutralizing vaccine
14. Vaccine examples 1 through 13 can be further modified by the addition of CD40L, either admixed or bound to the multivalent carrier
15. Vaccine examples 1 through 14 can be further modified by the addition of one or more cytokines other than GM-CSF, IL-3, or INF-γ, such as IL-1 + IL-2, either admixed or bound to the multivalent carrier

*The cytokine can be GM-CSF, IL-3, IFN-γ, or a combination thereof.

In sum, the experimental results show that IL-3 and/or GM-CSF stimulate the release of antibody by B cells and that, in combination, these cytokines act synergistically to stimulate the release of antibody by B cells. This induction is specifically inhibited by anti-IL-3 and anti-GM-CSF antibodies, respectively. The stimulatory effect of IFN-γ added 24 hours after culture is also shown.

The effects of IL-3 and GM-CSF are enhanced by multivalent antigen receptor cross-linkage, as mediated by dextran-conjugated anti-Ig antibody in the experimental model. The effects of IL-3 and GM-CSF may also be enhanced with antigen that does not induce high levels of membrane Ig cross-linking. Although both dextran-conjugated anti-Ig antibody and IL-1+IL-2 are required for optimal IL-3- and GM-CSF-mediated Ig secretion, both IL-3 and GM-CSF stimulate a modest Ig secretory response by cells activated with dextran-conjugated anti-Ig antibody alone. This is the first report demonstrating the ability of IL-3 and GM-CSF to act directly as differentiation factors for B cells.

In addition, while maximal antibody secretion is obtained with the use of GM-CSF, IL-3, IL-1+IL-3, and IFN-γ added 24 hours after culture, a modest increase in antibody secretion was also observed with the sole addition of IFN-γ 24 hours after culture.

Having now fully described the invention, it will be apparent to one of ordinary skill in the art that many changes and modifications can be made thereto without departing from the spirit or scope of the invention as set forth herein. The appended claims are not intended to be limiting.

We claim:

1. An in vitro assay system for identifying compositions useful for stimulating the release of antibody by B cells comprising:

a) dextran conjugated to anti-immunoglobin antibodies, wherein said anti-immunoglobin antibodies are directed against IgD or IgM; and b) a highly purified population of B cells, wherein said population is more than 99% B cells.

2. An in vitro method for identifying compositions useful for stimulating the release of antibody by B cells comprising:

a) providing an assay system comprising
      1) dextran conjugated to anti-immunoglobin antibodies, wherein said anti-immunoglobin antibodies are directed against IgD or IgM; and
      2) a highly purified population of B cells, wherein said population is more than 99% B cells, b) adding a sample composition to be tested; and c) detecting the secretion of Ig by B cells, wherein the secretion is indicative of the usefulness of the tested compound as an agent for stimulating the release of antibody by B cells.

3. The in vitro assay system of claim 1 wherein the B cells are electronically sorted.

4. The in vitro assay system of claim 3 further comprising at least one cytokine.

5. The in vitro assay system of claim 4 wherein the cytokine is selected from the group consisting of IL-1, IL-2, IL-3, GM-CSF, IFN-γ.

6. The in vitro method of claim 2 wherein the B cells are electronically sorted.

7. The in vitro method of claim 6 further comprising at least one cytokine.

8. The in vitro method of claim 7, wherein the cytokine is selected from the group consisting of IL-1, IL-2, IL-3, GM-CSF, IFN-γ.

* * * * *